(12) United States Patent
Moneuze et al.

(10) Patent No.: US 9,078,820 B2
(45) Date of Patent: *Jul. 14, 2015

(54) OIL-IN-WATER EMULSION CONTAINING AN AMPHIPHILIC POLYMER AND A SILICONE ELASTOMER

(75) Inventors: Gaelle Moneuze, Paris (FR); Thierry Cotton, Paris (FR); Brigitte Lavaud, Paris (FR)

(73) Assignee: L'OREAL, Paris (FR)

( * ) Notice: Subject to any disclaimer, the term of this patent is extended or adjusted under 35 U.S.C. 154(b) by 354 days.

This patent is subject to a terminal disclaimer.

(21) Appl. No.: 12/613,679

(22) Filed: Nov. 6, 2009

(65) Prior Publication Data

US 2010/0221296 A1    Sep. 2, 2010

Related U.S. Application Data

(60) Provisional application No. 61/117,583, filed on Nov. 25, 2008.

(30) Foreign Application Priority Data

Nov. 7, 2008    (FR) ...................................... 08 57570

(51) Int. Cl.
*A61Q 19/00* (2006.01)
*A61K 8/06* (2006.01)
*A61K 8/25* (2006.01)
*A61K 8/42* (2006.01)
*A61K 8/81* (2006.01)
*A61K 8/895* (2006.01)

(52) U.S. Cl.
CPC . *A61K 8/06* (2013.01); *A61K 8/062* (2013.01); *A61K 8/8158* (2013.01); *A61K 8/895* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2003/0157047 A1* | 8/2003 | Lennon et al. | 424/70.11 |
| 2003/0171479 A1 | 9/2003 | Lennon | |
| 2005/0002891 A1* | 1/2005 | Aubrun-Sonneville et al. | 424/70.17 |
| 2005/0053568 A1 | 3/2005 | Aubrun-Sonneville et al. | |
| 2005/0220728 A1* | 10/2005 | Kanji et al. | 424/59 |
| 2008/0226577 A1 | 9/2008 | L'Alloret et al. | |

FOREIGN PATENT DOCUMENTS

| | | |
|---|---|---|
| EP | 1 055 406 | 11/2000 |
| EP | 1 414 655 | 5/2004 |
| EP | 1 415 645 | 5/2004 |
| JP | 2003-277222 | 10/2003 |
| JP | 2003-277222 A | 10/2003 |
| JP | 2004-315525 | 11/2004 |
| JP | 2004-315525 A | 11/2004 |
| JP | 2008-163023 | 7/2008 |
| JP | 2008-163023 A | 7/2008 |
| WO | WO 2007/141142 | 12/2007 |

OTHER PUBLICATIONS

Office Action issued Nov. 19, 2013 in Japanese Patent Application No. 2009-255292 (submitting English translation only).
Office Action as received in the corresponding Japanese Patent Application No. 2009-255292 dated Oct. 20, 2014.

* cited by examiner

*Primary Examiner* — H. Sarah Park
(74) *Attorney, Agent, or Firm* — Oblon, McClelland, Maier & Neustadt, L.L.P.

(57) ABSTRACT

Composition in the form of an oil-in-water emulsion containing an oily phase dispersed in an aqueous phase, characterized in that it contains at least one (uncrosslinked) amphiphilic polymer and at least one organopolysiloxane elastomer.

14 Claims, No Drawings

OIL-IN-WATER EMULSION CONTAINING AN AMPHIPHILIC POLYMER AND A SILICONE ELASTOMER

REFERENCE TO PRIOR APPLICATIONS

This application claims priority to U.S. provisional application Ser. No. 61/117,583, filed Nov. 25, 2008; and to French patent application 08 57570, filed Nov. 7, 2008, both incorporated herein by reference.

FIELD OF THE INVENTION

The present application relates to a composition in the form of an oil-in-water emulsion containing at least one particular amphiphilic polymer. Preferably, the composition also contains at least one organopolysiloxane elastomer.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For various reasons linked in particular to better comfort during use (softness, emollience and others), current cosmetic compositions are usually in the form of an emulsion of the oil-in-water (O/W) type composed of an aqueous dispersing continuous phase and of an oily dispersed discontinuous phase or of an emulsion of the water-in-oil (W/O) type composed of an oily dispersing continuous phase and of an aqueous dispersed discontinuous phase. W/O emulsions are the most in demand in the cosmetics field due to the fact that they comprise, as an external phase, an aqueous phase which gives them, during the application to the skin, a fresher, less greasy and lighter feel than W/O emulsions.

Moreover, in order to improve the feel properties of these emulsions, it is possible to use silicone elastomers; these compounds provide softness but may be difficult to stabilize in the emulsion and require the use of surfactants.

However, the addition of surfactants leads to a loss of transparency of the product since the emulsion generally has a size of the oil drops or oily globules that is around one micron. These oily globules therefore strongly scatter the light and the emulsion then has a white colour.

Emulsions are known, for example from document EP 1 415 645, which comprise a silicone elastomer and crosslinked AMPS-derived amphiphilic polymers such as the products sold under the name Hostacerin AMPS sold by Hoechst. These crosslinked polymers result in emulsions that have a more translucent appearance but which are difficult to stabilize in the case where it is desired to obtain fluid textures, since a phenomenon of creaming of the emulsion occurs.

There is therefore a need to produce oil-in-water emulsions that have a satisfactory translucent appearance, confer a soft, fresh and light feel on the skin, give a non-greasy effect to the skin and that are stable whatever their viscosity and can therefore be formulated in a wide range of textures (sprayable fluid to thick cream).

DETAILED DESCRIPTION OF THE PREFERRED EMBODIMENTS

It has now surprisingly been discovered that oil-in-water emulsions that comprise at least one uncrosslinked AMPS-derived amphiphilic polymer and an organopolysiloxane elastomer respond to this need and others. The emulsions obtained are translucent and can just as easily be in the form of fluids as thick creams. They are, in particular embodiments, in the form of an emulsified gel.

Thus, the present invention relates to a composition preferably suitable for topical application, in the form of an oil-in-water emulsion, comprising an oily phase dispersed in an aqueous phase, characterized in that it comprises:

at least one uncrosslinked amphiphilic polymer comprising:

(a) from 80 to 99 mol % of 2-acrylamido-2-methylpropanesulphonic acid (AMPS) units of formula (3) below:

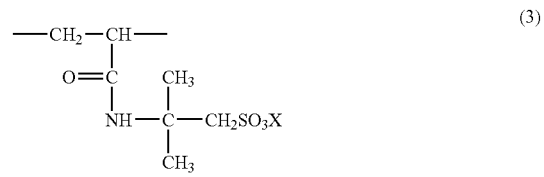

(3)

in which X is a proton, an alkali metal cation, an alkaline-earth metal cation or an ammonium ion; it may be understood that when X represents an alkaline-earth metal cation, it shares two positive charges with two $SO_3$ groups;

(b) and from 1 to 20 mol %, and preferably from 1 to 15 mol %, of units of formula (3a) below:

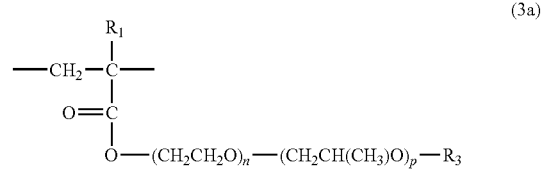

(3a)

in which n and p, independently of one another, denote a number of moles and vary from 0 to 30 on condition that n+p is less than or equal to 30; $R_1$ denotes a hydrogen atom, or a linear or branched $C_1$-$C_6$ alkyl radical and $R_3$ denotes a linear or branched alkyl group comprising m carbon atoms ranging from 6 to 30; and at least one organopolysiloxane elastomer.

The expression "topical application" is understood here to mean external application to keratin materials, which include, in particular, the skin, the scalp, the eyelashes, the eyebrows, the nails, mucous membranes and the hair.

Since the composition according to the invention is preferably intended for a topical application, it preferably contains or constitutes a physiologically acceptable medium, that is to say one that is compatible with the keratin materials such as the skin, mucous membranes, keratin fibres such as the eyelashes, the hair and the scalp.

The composition according to the invention has the advantage of being satisfactorily harmless and of having good cosmetic properties, that is to say a texture that is homogeneous and that is pleasant on application. Moreover, it is very stable over time. An emulsion is stable if no change in its macroscopic or microscopic appearance and in its physicochemical characteristics (size of the drops, pH, viscosity) is observed after storing at ambient temperature for a period of 15 days.

The composition according to the invention advantageously has an average size of the oily globules that ranges from 15 to 500 µm.

The average size of the oily globules may be measured using a Leica DM LB2 type microscope with a lens enabling a ×10 magnification, according to the following protocol: a spot of the product to be measured is deposited on a glass slide using a fine spatula, then a coverglass is pressed over the sample. The sample thus prepared is observed visually via the lens of the microscope.

The drops whose size is the most representative of the population observed are located therein by moving over the sample.

Using the image processing software of the microscope, the diameter of the drop located is then measured with a slide directly on the screen of the computer connected to the microscope. This diameter is the average diameter or average size of the oily globules of the emulsion.

The minimum diameter and the maximum diameter of the population of the globules of the sample in question are defined in the same manner.

The average size of the oily globules may range from 15 to 500 µm, preferably from 15 to 300 µm and better still from 15 to 250 µm.

The emulsions according to the invention are translucent, in particular, they have a light transmission at a wavelength equal to 500 nm, through a sample having a thickness of 50 µm, of at least 1.5 times higher than an emulsion of the same composition for which the diameter of the drops is less than 15 µm. The transmission is measured using a Carry 600 UV/Visible spectrophotometer at a wavelength equal to 500 nm. The emulsion is placed between two quartz slides having a thickness of 0.05 mm, one of which comprises a notch with a depth of 50 microns.

The viscosity of the dispersions obtained may range from very fluid to very viscous (cream) and it is adjusted, in particular, as a function of the polymer content introduced and of the amount of emulsified oily phase. The composition of the invention has a viscosity which may range, for example, from 0.01 Pa·s to 100 Pa·s at a temperature of 25° C., the viscosity being measured using a Rheomat 180 (Lamy), equipped with an MS-R1, MS-R2, MS-R3, MS-R4 or MS-R5 spindle chosen as a function of the consistency of the composition, rotating at a rotational speed of 200 rpm.

Another subject of the invention is a method for the treatment of keratin materials, characterized in that a composition as described above is applied to the keratin materials.

According to another aspect, one subject of the invention is the use of the combination
of at least one uncrosslinked amphiphilic polymer comprising:
(a) from 80 to 99 mol % of 2-acrylamido-2-methylpropanesulphonic acid (AMPS) units of formula (3) below:

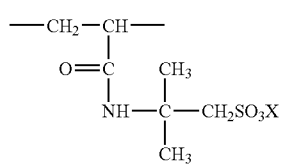

(3)

in which $X^+$ is a proton, an alkali metal cation, an alkaline-earth metal cation or an ammonium ion; it may be understood that when X represents an alkaline-earth metal cation, it shares two positive charges with two $SO_3$ groups;
(b) and from 1 to 20 mol %, and preferably from 1 to 15 mol %, of units of formula (3a) below:

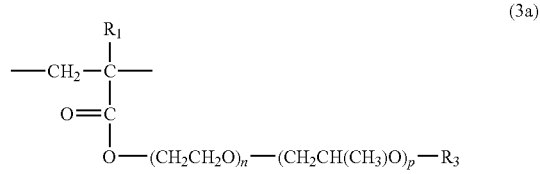

(3a)

in which n and p, independently of one another, denote a number of moles and vary from 0 to 30 on condition that n+p is less than or equal to 30; $R_1$ denotes a hydrogen atom, or a linear or branched $C_1$-$C_6$ alkyl radical and $R_3$ denotes a linear or branched alkyl group comprising m carbon atoms ranging from 6 to 30; and
at least one organopolysiloxane elastomer, in order to obtain a translucent oil-in-water emulsion.

Amphiphilic Polymer

The amphiphilic polymer used in the composition according to the invention is a polymer derived from 2-acrylamido-2-methylpropanesulphonic acid (AMPS) comprising:
(a) from 80 to 99 mol % of 2-acrylamido-2-methylpropanesulphonic acid (AMPS) units of formula (3) below:

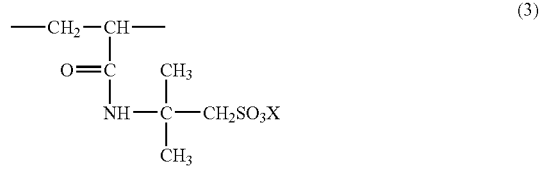

(3)

in which $X^+$ is a proton, an alkali metal cation, an alkaline-earth metal cation or an ammonium ion; it may be understood that when X . represents an alkaline-earth metal cation, it shares two positive charges with two $SO_3$ groups;
(b) and from 1 to 20 mol %, and preferably from 1 to 15 mol %, of units of formula (3a) below:

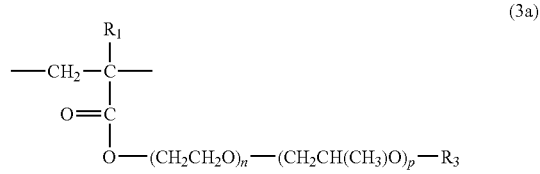

(3a)

in which n and p, independently of one another, denote a number of moles and vary from 0 to 30, preferably from 1 to 20 on condition that n+p is less than or equal to 30, preferably less than 25 and better still less than 20; $R_1$ denotes a hydrogen atom, or a linear or branched $C_1$-$C_6$ alkyl (preferably methyl) radical and $R_3$ denotes a linear or branched alkyl group comprising m carbon atoms ranging from 6 to 30, preferably from 10 to 25 carbon atoms.

The expression "amphiphilic polymer" is understood to mean a polymer which comprises at least one hydrophilic part (or block) and at least one hydrophobic part (or block). This polymer is water-soluble or water-dispersible.

The amphiphilic polymers used in the composition of the invention are water-soluble or water-dispersible. The expression "water-soluble or water-dispersible polymer" is understood to mean a polymer which, introduced into water at a concentration equal to 1% by weight, results in a macroscopically homogeneous solution for which the light transmission, at a wavelength equal to 500 nm, through a sample having a thickness of 1 cm, is at least 10%, which corresponds to an absorbance [abs=−log (transmission)] of less than 1.5.

The amphiphilic polymers according to the invention preferably have, in general, a weight-average molecular weight ranging from 50 000 to 10 000 000, more preferably from 100 000 to 8 000 000 and more preferably still from 200 000 to 3 000 000.

The polymers according to the invention are preferably partially or completely neutralized by a mineral base such as, for example, sodium hydroxide, potassium hydroxide, or ammonium hydroxide, or by an organic base such as mono-, di- and triethanolamine, aminomethylpropanediol, N-methylglucamine, basic amino acids such as arginine and lysine, and mixtures thereof.

The polymers used in accordance with the invention can be obtained according to conventional radical polymerization processes in the presence of one or more initiators, such as, for example, azobisisobutyronitrile (AIBN), azobisdimethylvaleronitrile, 2,2'-azo-bis[2-amidinopropane]hydrochloride (ABAH), organic peroxides, such as dilauryl peroxide, benzoyl peroxide, tert-butyl hydroperoxide etc., inorganic peroxide compounds, such as potassium persulphate or ammonium persulphate, or $H_2O_2$, optionally in the presence of reducing agents.

The polymers are obtained in particular by radical polymerization in a tert-butanol medium from which they precipitate. It is possible, by using polymerization in tert-butanol, to obtain a distribution in the size of the polymer particles which is particularly favourable for the uses of the polymer.

The polymerization reaction can be carried out at a temperature of between 0° C. and 150° C., preferably between 20° C. and 100° C., either at atmospheric pressure or under reduced pressure. It can also be carried out under an inert atmosphere, preferably under nitrogen.

The amphiphilic AMPS polymers used in the composition according to the invention are preferably uncrosslinked.

Mention may be made, as polymers derived from AMPS which can be used in the composition according to the invention, of the polymers prepared from 2-acrylamido-2-methylpropanesulphonic acid (AMPS) or one of its sodium or ammonium salts with an ester of (meth)acrylic acid and of an oxyethylenated $C_{10}$ to $C_{20}$ alcohol comprising from 6 to 25 oxyethylenated groups.

Mention may in particular be made of the polymers prepared from 2-acrylamido-2-methylpropanesulphonic acid (AMPS) or one of its sodium or ammonium salts, with an ester of (meth)acrylic acid and:

of a $C_{10}$-$C_{18}$ alcohol oxyethylenated with 8 mol of ethylene oxide (Genapol C-080 from Clariant);
of a $C_{11}$ oxo alcohol oxyethylenated with 8 mol of ethylene oxide (Genapol UD-080 from Clariant);
of a $C_{11}$ oxo alcohol oxyethylenated with 7 mol of ethylene oxide (Genapol UD-070 from Clariant);
of a $C_{12}$-$C_{14}$ alcohol oxyethylenated with 7 mol of ethylene oxide (Genapol LA-070 from Clariant);
of a $C_{12}$-$C_{14}$ alcohol oxyethylenated with 9 mol of ethylene oxide (Genapol LA-090 from Clariant);
of a $C_{12}$-$C_{14}$ alcohol oxyethylenated with 11 mol of ethylene oxide (Genapol LA-110 from Clariant);
of a $C_{16}$-$C_{18}$ alcohol oxyethylenated with 8 mol of ethylene oxide (Genapol T-080 from Clariant);
of a $C_{16}$-$C_{18}$ alcohol oxyethylenated with 11 mol of ethylene oxide (Genapol T-110 from Clariant);
of a $C_{16}$-$C_{18}$ alcohol oxyethylenated with 15 mol of ethylene oxide (Genapol T-150 from Clariant);
of a $C_{16}$-$C_{18}$ alcohol oxyethylenated with 20 mol of ethylene oxide (Genapol T-200 from Clariant);
of a $C_{16}$-$C_{18}$ alcohol oxyethylenated with 25 mol of ethylene oxide (Genapol T-250 from Clariant);
of a $C_{18}$-$C_{22}$ alcohol oxyethylenated with 25 mol of ethylene oxide; and
of a $C_{16}$-$C_{18}$ iso alcohol oxyethylenated with 25 mol of ethylene oxide.

According to a preferred embodiment, the amphiphilic polymer is a copolymer of AMPS and of a methacrylate of a $C_{16}$-$C_{18}$ alcohol comprising from 6 to 25 oxyethylenated groups, obtained from methacrylic acid or from a methacrylic acid salt and from a $C_{16}$-$C_{18}$ alcohol oxyethylenated with 6 to 25 mol of ethylene oxide. The amphiphilic polymer can also be a copolymer of AMPS and of a methacrylate of a $C_{12}$-$C_{14}$ alcohol comprising from 6 to 25 oxyethylenated groups, obtained from methacrylic acid or from a methacrylic acid salt and from a $C_{12}$-$C_{14}$ alcohol oxyethylenated with 6 to 25 mol of ethylene oxide.

Mention may be made, as amphiphilic polymers preferred according to the present invention, of:

the uncrosslinked copolymer obtained from 92.65 mol % of AMPS and 7.35 mol % of a methacrylate of a $C_{16}$-$C_{18}$ alcohol comprising 8 oxyethylenated groups (Genapol T-080), such as that sold by Clariant under the name Aristoflex SNC;
the uncrosslinked copolymer obtained from 91.5 mol % of AMPS and 8.5 mol % of a methacrylate of a $C_{12}$-$C_{14}$ alcohol comprising 7 oxyethylenated groups (Genapol LA-070), such as that sold by Clariant under the name Aristoflex LNC;
and blends thereof.

These copolymers are appropriate for giving stable emulsions which are provided under highly varied textures, ranging from sprayable fluid to cream, with very good cosmetic qualities.

These polymers exhibit the advantage of being relatively insensitive to pH variations for values of between 4 and 8, which are the normal values of cosmetic compositions.

The amount (as active material) of (uncrosslinked) amphiphilic polymer as described above in the composition according to the invention is not limited and may range in particular from 0.01 to 10% by weight relative to the total weight of the composition, preferably from 0.05 to 5% by weight and better still from 0.1 to 3% by weight. Of course, and as with all composition components, ingredients, additives, etc., described herein, the invention composition may comprise one or more such materials, in this case one or more amphiphilic polymers.

Organopolysiloxane Elastomer

The composition of the invention contains at least one organopolysiloxane elastomer, also sometimes referred to as "silicone elastomer" in the remainder of the description, preferably that is at least partially crosslinked. The term "elastomer" is understood to mean a flexible and deformable solid material having visco-elastic properties and in particular the consistency of a sponge or of a flexible sphere. Its modulus of elasticity is such that this material withstands deformation and has a limited ability to expand and to contract. This material is capable of returning to its original shape after it has been stretched. This elastomer is formed of high molecular weight polymer chains, the mobility of which is limited by a uniform network of crosslinking points.

The organopolysiloxane elastomers used in the composition according to the invention are preferably partially or completely crosslinked. They are in the form of particles. In particular, the particles of organopolysiloxane elastomer have a size ranging from 0.1 to 500 μm, preferably from 3 to 200 μm and better still from 3 to 50 μm. These particles may have any shape and, for example, may be spherical, flat or amorphous.

When they are included in an oily phase, these organopolysiloxane elastomers are converted, depending on the amount of oily phase used, into a product having a spongy appearance when they are used in the presence of low oily phase contents, or into a homogeneous gel in the presence of larger amounts of oily phase. The gelling of the oily phase by these elastomers may be complete or partial.

Thus, the elastomers of the invention may be transported in the form of an anhydrous gel composed of an organopolysiloxane elastomer and of an oily phase. The oily phase used during the manufacture of the anhydrous gel of organopolysiloxane elastomer contains one or more oils that are liquid at ambient temperature (25° C.) chosen from hydrocarbon-based oils and/or silicone oils. Advantageously, the oily phase is a silicone liquid phase, containing one or more oils chosen from polydimethylsiloxanes having a linear or cyclic chain, which are liquid at ambient temperature, optionally comprising an alkyl or aryl chain that is pendent or that is at the end of the chain, the alkyl chain having from 1 to 6 carbon atoms.

The organopolysiloxane elastomers used according to the invention may be chosen from the crosslinked polymers described in Application EP-A-0 295 886 and from those described in U.S. Pat. No. 5,266,321. They are preferably non-emulsifying. The expression "non-emulsifying organopolysiloxane elastomers" defines organopolysiloxane elastomers that do not contain a hydrophilic chain such as polyoxyalkylene or polyglycerolated units.

The silicone elastomer is a crosslinked organopolysiloxane elastomer which may be obtained by crosslinking addition reaction of a diorganopolysiloxane containing at least one hydrogen bonded to the silicon and of a diorganopolysiloxane having ethylenically unsaturated groups bonded to the silicon, especially in the presence of a platinum catalyst; or by dehydrogenation crosslinking condensation reaction between a diorganopolysiloxane having hydroxyl end groups and a diorganopolysiloxane containing at least one hydrogen bonded to the silicon, especially in the presence of an organotin compound; or by crosslinking condensation reaction of a diorganopolysiloxane having hydroxyl end groups and of a hydrolysable organopolysilane; or by thermal crosslinking of an organopolysiloxane, especially in the presence of an organoperoxide catalyst; or by crosslinking of an organopolysiloxane by high-energy radiation such as gamma rays, ultraviolet rays or an electron beam.

Preferably, the crosslinked organopolysiloxane elastomer is obtained by crosslinking addition reaction (A) of a diorganopolysiloxane containing at least two hydrogen atoms each bonded to a different silicon atom, and (B) of a diorganopolysiloxane having at least two ethylenically unsaturated groups bonded to the silicon, especially in the presence (C) of a platinum catalyst, as described, for example, in Application EP-A-295 886.

In particular, the organopolysiloxane may be obtained by reaction of a dimethylpolysiloxane having dimethylvinylsiloxy end groups and of a methylhydrogenpolysiloxane having trimethylsiloxy end groups, in the presence of a platinum catalyst.

The compound (A) is the base reactant for the formation of an organopolysiloxane elastomer and the crosslinking is carried out by an addition reaction of the compound (A) with the compound (B) in the presence of the catalyst (C).

The compound (A) is advantageously a diorganopolysiloxane having at least two lower (for example $C_2$-$C_4$) alkenyl groups; the lower alkenyl group may be chosen from vinyl, allyl and propenyl groups. These lower alkenyl groups may be located at any position on the organopolysiloxane molecule but are preferably located at the ends of the organopolysiloxane molecule. The organopolysiloxane (A) may have a branched chain, linear chain, cyclic or network structure but the linear chain structure is preferred. The compound (A) may have a viscosity ranging from the liquid state to the gum state. Preferably, the compound (A) has a viscosity of at least 100 centistokes at 25° C.

The organopolysiloxanes (A) may be chosen from methylvinylsiloxanes, methylvinylsiloxane/dimethylsiloxane copolymers, dimethylpolysiloxanes having dimethylvinylsiloxy end groups, dimethylsiloxane/methylphenylsiloxane copolymers having dimethylvinylsiloxy end groups, dimethylsiloxane/diphenylsiloxane/methylvinylsiloxane copolymers having dimethylvinylsiloxy end groups, dimethylsiloxane/methylvinylsiloxane copolymers having trimethylsiloxy end groups, dimethylsiloxane/methylphenylsiloxane/methylvinylsiloxane copolymers having trimethylsiloxy end groups, methyl(3,3,3-trifluoropropyl)polysiloxanes having dimethylvinylsiloxy end groups and dimethylsiloxane/methyl(3,3,3-trifluoropropyl)siloxane copolymers having dimethylvinylsiloxy end groups.

The compound (B) is, in particular, an organopolysiloxane having at least two hydrogens bonded to the silicon in each molecule and is therefore the crosslinking agent of the compound (A).

Advantageously, the sum of the number of ethylenic groups per molecule of the compound (A) and the number of hydrogen atoms bonded to the silicon per molecule of the compound (B) is at least 4.

The compound (B) may have any molecular structure, in particular a linear chain or branched chain structure or a cyclic structure.

The compound (B) may have a viscosity, at 25° C., ranging from 1 to 50 000 centistokes, especially in order to be highly miscible with the compound (A).

It is advantageous for the compound (B) to be added in an amount such that the molecular ratio between the total amount of hydrogen atoms bonded to the silicon in the compound (B) and the total amount of all the ethylenically unsaturated groups in the compound (A) is within the range of 1/1 to 20/1.

The compound (B) may be chosen from methylhydrogenpolysiloxanes having trimethylsiloxy end groups, dimethylsiloxane/methylhydrogensiloxane copolymers having trimethylsiloxy end groups and cyclic dimethylsiloxane/methylhydrogensiloxane copolymers.

The compound (C) is the catalyst of the crosslinking reaction, and is especially chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added in an amount of 0.1 to 1000 parts by weight, better still from 1 to 100 parts by weight, as actual platinum metal per 1000 parts by weight of the total amount of the compounds (A) and (B).

Other organic groups may be bonded to the silicon in the organopolysiloxanes (A) and (B) described previously, such as for example alkyl groups such as methyl, ethyl, propyl, butyl or octyl groups; substituted alkyl groups such as 2-phenylethyl, 2-phenylpropyl or 3,3,3-trifluoropropyl groups; aryl groups such as phenyl, tolyl or xylyl groups; substituted aryl groups such as a phenylethyl group; and substituted monovalent hydrocarbon-based groups such as an epoxy group, a carboxylate ester group or a mercapto group.

The non-emulsifying silicone elastomer is generally mixed with at least one hydrocarbon-based oil and/or one silicone oil in order to form a gel. In these gels, the non-emulsifying elastomer is in the form of non-spherical particles.

The organopolysiloxane elastomers used in the composition of the invention may be, for example, those sold under the names KSG 6 by Shin-Etsu; Trefil E-505C or Trefil E-506C by Dow Corning; Gransil (SR-CYC, SR DMF10, SR-DC556) by Grant Industries, or those sold in the form of gels that are already formed: KSG 15, KSG 16, KSG 17, KSG 18, KSG 26A, KSG 26B, KSG-31, KSG-32, KSG-33, KSG-41, KSG-42, KSG-43 and KSG-44 from Shin-Etsu; Gransil SR 5CYC gel, Gransil SR DMF 10 gel, Gransil SR DC556 gel and Gransil RPC from Grant Industries; 1229-02-167 and 1229-02-168 from General Electric.

According to one preferred embodiment, silicone elastomers bearing the INCI name dimethicone/vinyldimethicone copolymer (or polysilicone-11) are used as a mixture with a cyclic silicone oil. Mention may be made, for example, of the mixture of crosslinked organopolysiloxane/cyclopentasiloxane or a mixture of crosslinked organopolysiloxane/cyclohexasiloxane such as, for example, Gransil RPS D5 or Gransil RPS D6 from Grant Industries.

Mention may also be made of the elastomers sold under the references DC 9040, DC 9041, DC 9509, DC 9505 and DC 9506 by Dow Corning. It is also possible to use a mixture of silicone elastomers, and especially a mixture of these commercial products.

The organopolysiloxane elastomer or elastomers used according to the invention are present in an amount, as active material, that varies depending on the intended purpose. This amount is not limited and may range, for example, from 0.01 to 100, preferably from 0.5 to 7% and better still from 1 to 4% of the total weight of the composition.

Emulsifiers

In order to facilitate the emulsification of the oily phase, the composition according to the invention can comprise one or more emulsifiers (separate from and different from the (uncrosslinked) amphiphilic polymer and organopolysiloxane elastomer), also known as "coemulsifiers".

The amount (as active material) of emulsifier(s) can range, for example, from 0.001% to 5% by weight, preferably from 0.005% to 2% by weight and better still from 0.01% to 1% by weight, relative to the total weight of the composition.

The emulsifier is preferably used in an amount of less than 20% by weight, relative to the weight of amphiphilic polymer.

The emulsifier is preferably used in an amount of less than or equal to 1% by weight relative to the weight of the composition, preferably less than or equal to 0.5% by weight and better still less than or equal to 0.1% by weight. According to one embodiment, the composition according to the invention is free of emulsifier or coemulsifier.

The emulsifier can be chosen from alkylpolyglucosides, polyoxyethylene (POE) alkyl esters or ethers, glycerol alkyl esters or ethers, oxyethylenated or nonoxyethylenated sorbitan alkyl esters or ethers, dimethicone copolyols, gemini surfactants or mono- or disodium acylglutamates.

Mention may in particular be made of:

glycerol esters, such as glycerol mono- or polyalkyl esters or ethers, such as described in the documents EP 1 010 416 and EP 1 010 414, glyceryl monoisostearate, such as the product sold under the name Peceol Isostéarique by Gattefossé, the polyglycerolated (4 mol) isostearate sold under the name Isolan GI34 by Goldschmidt, the polyglycerolated (3 mol) diisostearate sold under the name Lameform TGI by Cognis and the polyglycerolated (2 mol) distearate sold under the name Emalex PGSA by Nihon Emulsion.

polyethylene glycol esters and ethers, such as polyethylene glycol alkyl esters and ethers, such as described in the documents EP 1 120 101 and EP 1 016 453, Oleth-50, sold under the name Emalex 550 by Nihon Emulsion, Oleth-20, sold under the name Brij 98 by Uniqema, Ceteth-2 and Ceteth-10, sold under the names Brij 52 and 56 by Uniqema, Laureth-23, sold under the name Brij 35 by Uniqema, PEG-8 stearate, sold under the name Myrj 45 by Uniqema, PEG-8 isostearate, such as the product sold under the name Prisorine 3644 by Uniqema, and PEG-20 stearate and PEG-40 stearate, sold under the names Myrj 49 and Myrj 52 by Uniqema.

Mention may also be made of the following compounds, sold by Uniqema:

| Trade name | INCI name |
| --- | --- |
| Brij 35 | Laureth-23 |
| Brij 30 | Laureth-4 |
| Brij 96 | Oleth-10 |
| Brij 56 | Ceteth-10 |
| Brij 98 | Oleth-20 |
| Brij 76 | Steareth-10 |
| Brij 72 | Steareth-2 |
| Brij 52 | Ceteth-2 |
| Brij 78 | Steareth-20. | sorbitan esters or ethers, such as oxyethylenated or nonoxyethylenated sorbitan mono- or polyalkyl esters or ethers, such as described in the document EP 1 010 415, or also the following products, sold by Uniqema:

| Examples: | Trade name | INCI name |
| --- | --- | --- |
| | Tween 21 | Polysorbate 21 |
| | Tween 40 | Polysorbate 40 |
| | Tween 80 | Polysorbate 80 |
| | Tween 60V | Polysorbate 60 |
| | Tween 61V | Polysorbate 61. |

Mention is also made of sorbitan isostearate, such as the product sold under the name Arlacel 987 by Uniqema, glyceryl sorbitan isostearate, such as the product sold under the name Arlacel 986 by Uniqema, sorbitan sesquioleate, such as the product sold under the name Arlacel 83V by Uniqema, sorbitan laurate, sorbitan monopalmitate, sorbitan oleate, sorbitan trioleate, sorbitan monostearate and sorbitan tristearate, such as the products sold under the names Span 20, Span 40, Span 80V, Span 85V, Span 60 and Span 65V by Uniqema.

Sugar mono- or polyalkyl esters or ethers, such as the mono- or polyalkyl esters or ethers of sugars as described in the U.S. Pat. No. 6,689,371. Mention may be made, for example, of methyl glucose isostearate, such as Isolan-IS from Degussa Goldschmidt, or also sucrose distearate, such as Crodesta F50, sold by Croda, and sucrose stearate, such as Ryoto Sugar Ester S 1570, sold by Mitsubishi Kagaku Foods.

Alkoxylated alkenyl succinates, for example as described in the document EP 1 025 898.

Fatty alcohols, such as fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol and their mixtures.

Silicone derivatives, such as dimethicone copolyols, for example the mixture of cyclomethicone and of dimethicone copolyol sold under the name DC 5225 C by Dow Corning, and alkyl dimethicone copolyols, such as lauryl methicone copolyol, sold under the name Dow Corning 5200 Formulation Aid by Dow Corning, and cetyl dimethicone copolyol, sold under the name Abil EM 90 by Goldschmidt, or the polyglyceryl-4 isostearate/cetyl dimethicone copolyol/hexyl laurate mixture sold under the name Abil WE 90 by Goldschmidt.

Alkoxylated alkenyl succinates, such as, for example, those which are described in the document EP 1 025 898.

Alkyl phosphoric esters, such as, for example, those which are described in the document EP 1 013 338.

Alkyl ether citrates, such as, for example, those which are described in the document EP 1 020 219.

Lipoamino acids and their salts, such as mono- and disodium acylglutamates, such as, for example, monosodium stearoyl glutamate (Amisoft HS-11PF) and disodium stearoyl glutamate (Amisoft HS-21P), sold by Ajinomoto.

Alkyl phosphates and their salts, such as the alkali metal salts of dicetyl and dimyristyl phosphate, or also potassium cetyl phosphate, such as Amphisol K, sold by DSM Nutritional Products.

Cholesterol derivatives, such as the alkali metal salts of cholesterol sulphate or the alkali metal salts of cholesterol phosphate.

Ammonium salts of phosphatidic acid.

Phospholipids.

Alkylsulphonic derivatives, such as described in the patent document EP 1 120 101.

According to a preferred form of the invention, the coemulsifier is chosen from glyceryl esters (glyceryl isostearate), sorbitan esters (Polysorbate 60) and polyethylene glycol esters (PEG 8 isostearate).

Aqueous Phase

The aqueous phase of the composition according to the invention comprises water and optionally one or more compounds which are miscible with water or at least partially miscible with water, such as polyols; or lower $C_2$ to $C_8$ monoalcohols, such as ethanol and isopropanol. The term "ambient temperature" should be understood as meaning a temperature of approximately 25° C. at standard atmospheric pressure (760 mmHg).

The term "polyol" should be understood as meaning any organic molecule comprising at least two free hydroxyl groups. Mention may be made, as polyols, for example, of glycols, such as butylene glycol, propylene glycol, isoprene glycol, glycerol and polyethylene glycols, such as PEG-8, sorbitol or sugars, such as glucose.

The aqueous phase can also comprise any normal water-soluble or water-dispersible additive as indicated below.

The aqueous phase can represent from 50 to 98% by weight, preferably from 55 to 95% by weight, better still from 60 to 90% by weight relative to the total weight of the composition.

The water-miscible compound or compounds, such as polyols and lower alcohols, can be present in an amount ranging for example from 0 to 30% of the total weight of the composition, in particular from 0.1 to 30% and better still in an amount ranging from 1 to 20%.

Oily Phase

The nature of the oily phase of the emulsion according to the invention is not limited. The oily phase is a fatty phase comprising at least one fatty substance chosen from fatty substances which are liquid at ambient temperature (20-25° C.) or volatile or non-volatile oils of vegetable, mineral or synthetic origin, and their mixtures. These oils are physiologically acceptable.

In the present invention, the amount of oily phase does not include the amount of emulsifiers which may be used according to the invention.

The oily phase can also comprise any normal fat-soluble or fat-dispersible additive as indicated below. It can in particular comprise other fatty substances, such as waxes, pasty compounds, fatty alcohols or fatty acids. The oily phase comprises at least one oil, more particularly at least one cosmetic oil. The term "oil" is understood to mean a fatty substance which is liquid at ambient temperature (25° C.)

Mention may be made, as oils which can be used in the composition of the invention, for example, of:

hydrocarbon oils of animal origin, such as perhydrosqualene;

hydrocarbon oils of vegetable origin, such as liquid triglycerides of fatty acids comprising from 4 to 10 carbon atoms, such as triglycerides of heptanoic acid or octanoic acid, or also, for example, sunflower, maize, soybean, pumpkin, grape seed, sesame, hazelnut, apricot, macadamia, arara, coriander, castor or avocado oils, triglycerides of caprylic/capric acids, such as those sold by Stéarineries Dubois or those sold under the names Miglyol 810, 812 and 818 by Dynamit Nobel, jojoba oil or shea butter oil;

synthetic esters and ethers, in particular of fatty acids, such as oils of formulae $R^1COOR^2$ and $R^1OR^2$ in which $R^1$ represents the residue of a fatty acid or of a fatty alcohol comprising from 8 to 29 carbon atoms and $R^2$ represents a branched or unbranched hydrocarbon-based chain comprising from 3 to 30 carbon atoms, such as, for example, purcellin oil, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as volatile or non-volatile liquid paraffins and their derivatives, liquid petrolatum, polydecenes, isohexadecane, isododecane or hydrogenated polyisobutene, such as Parleam® oil;

fluorinated oils which partially comprise hydrocarbon and/or silicone, such as those described in the document JP-A-2-295912;

silicone oils, such as volatile or non-volatile polydimethylsiloxanes (PDMSs) comprising a linear or cyclic silicone chain which are liquid or pasty at ambient temperature, in particular volatile silicone oils, especially cyclopolydimethylsiloxanes (cyclomethicones), such as cyclohexadimethylsiloxane and cyclopentadimethylsiloxane; polydimethylsiloxanes comprising pendent alkyl, alkoxy or phenyl groups or alkyl, alkoxy or phenyl groups at the end of the silicone chain, which groups have from 2 to 24 carbon atoms; or phenylated silicones, such as phenyltrimethicones, phenyldimethicones, phenyl(trimethylsiloxy) diphenylsiloxanes, diphenyldimethicones, diphenyl(methyldiphenyl)trisiloxanes, (2-phenylethyl)trimethylsiloxysilicates and polymethylphenylsiloxanes; mixtures thereof.

According to a preferred embodiment, the composition of the invention comprises at least one oil chosen from silicone oils, linear or branched hydrocarbons, synthetic ethers and esters, and mixtures thereof, in particular chosen from volatile silicone oils and branched hydrocarbons, such as Parleam® oil, and mixtures thereof.

The amount of oily phase can range, for example, from 1 to 40% by weight, preferably from 5 to 35% by weight, better still from 10 to 35% by weight relative to the total weight of the composition.

The amount of oily phase in the composition of the invention is preferably less than 40% by weight of the total weight of the composition, preferably less than or equal to 35% by weight and better still less than or equal to 33% by weight.

As indicated above, this amount of oily phase does not include the amount of emulsifier.

According to one embodiment, the composition according to the invention comprises less than 40% by weight of oils, relative to the total weight of the composition, in particular less than 35% by weight.

Additional Amphilic Polymer

According to one embodiment, the composition according to the invention comprises, besides the (uncrosslinked) amphiphilic polymer, a crosslinked amphiphilic polymer, which may be, in particular, chosen from hydrophobic modified crosslinked polymers of AMPS.

As hydrophobic modified crosslinked polymers of AMPS, it is possible to use, in particular, those comprising:

80 to 99 mol % and preferably from 85 to 99 mol % of 2-acrylamido-2-methylpropanesulphonic acid (AMPS) units of formula (I)

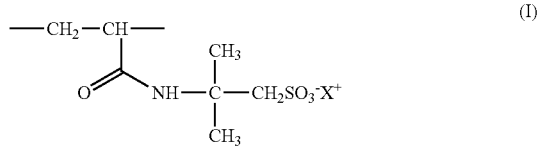

in which $X^+$ is a proton, an alkali metal cation, an alkaline-earth metal cation, an ammonium ion or an organic cation; and 1 to 20 mol % and preferably 1 to 15 mol % of hydrophobic units of formula (II) below:

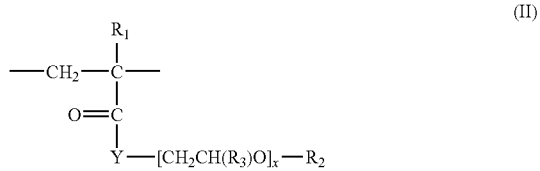

in which $R_1$ and $R_3$, which are identical or different, denote a hydrogen atom or a linear or branched $C_1$-$C_6$ alkyl (preferably methyl) radical; Y denotes O or NH; $R_2$ denotes a hydrocarbon-based radical comprising from 6 to 50 carbon atoms, more preferably from 6 to 22 carbon atoms, more preferably still from 6 to 18 carbon atoms and more particularly from 12 to 18 carbon atoms; x denotes a number of moles of alkylene oxide and varies from 0 to 100, and better still from 3 to 100.

The radical $R_2$ is preferably chosen from $C_6$-$C_{18}$ alkyl radicals that are substantially linear (for example, n-hexyl, n-octyl, n-decyl, n-hexadecyl, n-dodecyl or lauryl, n-octadecyl, stearyl or behenyl radicals), branched or cyclic (for example cyclododecane ($C_{12}$) or adamantane ($C_{10}$) radicals); $C_6$-$C_{18}$ perfluorinated alkyl radicals (for example, the group of formula —$(CH_2)_2$—$(CF_2)_9$—$CF_3$); the cholesteryl radical ($C_{27}$) or a residue of an ester of cholesterol such as the cholesteryl oxyhexanoate group; and aromatic polycyclic groups such as naphthalene or pyrene. Among these radicals, the linear alkyl radicals and more particularly the stearyl and behenyl radicals, and mixtures thereof are preferred.

According to one particularly preferred embodiment of the invention, the unit of formula (II) comprises at least one alkylene oxide unit ($x \geq 1$) and preferably several alkylene oxide units ($x > 1$) constituting a polyoxyalkylenated chain. The polyoxyalkylenated chain is preferably constituted of ethylene oxide units and/or propylene oxide units and more particularly still constituted of ethylene oxide units. The number of oxyalkylenated units (or number of moles of alkylene oxide) in general varies from 3 to 100, more preferably from 3 to 50 and more preferably still from 7 to 25.

Preferably, the polymer contains, as a hydrophobic unit of formula (II), a unit of formula (III):

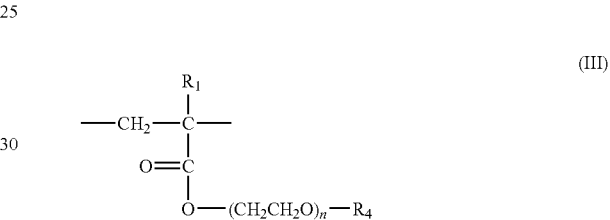

in which n denotes an integer that varies from 3 to 100, preferably from 3 to 50 and more preferably from 7 to 25; $R_1$ is a hydrogen or a methyl radical, and $R_4$ denotes a linear or branched alkyl radical comprising from 6 to 22 carbon atoms, preferably from 10 to 22 carbon atoms and better still from 14 to 22 carbon atoms.

The amphiphilic AMPS polymers which may be used in the composition according to the invention may be obtained according to conventional radical polymerization processes in the presence of one or more initiators, such as, for example, azobisisobutyronitrile (AIBN), azobisdimethylvaleronitrile, 2,2-azo-bis[2-amidinopropane]hydrochloride (ABAH), organic peroxides such as dilauryl peroxide, benzoyl peroxide, tert-butyl hydroperoxide, etc., inorganic peroxide compounds such as potassium or ammonium persulphate, or $H_2O_2$, optionally in the presence of reducing agents.

These hydrophobic modified polymers may especially be obtained by radical polymerization in a tert-butanol medium in which they precipitate. It is possible, by using precipitation polymerization in tert-butanol, to obtain a distribution in the size of the polymer particles which is particularly favourable for the uses of the polymer.

The reaction may be carried out at a temperature between 0 and 150° C., preferably between 10 and 100° C., either at atmospheric pressure or under reduced pressure. It may also be carried out under an inert atmosphere, preferably under nitrogen.

The crosslinked AMPS polymers used in the composition of the invention are preferably in partially or completely neutralized forms. The expression "partially neutralized polymers" is understood to mean polymers which are at least 90% neutralized. According to one preferred embodiment of the invention, they are completely neutralized.

Preferably, the partial or complete neutralization of the AMPS polymers used in accordance with the invention is carried out by means of an inorganic base (sodium hydroxide, potassium hydroxide, ammonium hydroxide) or an organic base such as mono-, di- or triethanolamine, an aminomethylpropanediol, N-methylglucamine, basic amino acids such as arginine and lysine, and mixtures of these compounds.

The polymers used are crosslinked. The crosslinking agents may be chosen from compounds having an olefinic polyunsaturation commonly used for crosslinking polymers obtained by radical polymerization.

Mention may be made, for example, as crosslinking agents, of divinylbenzene, diallyl ether, dipropylene glycol diallyl ether, polyglycol diallyl ethers, triethylene glycol divinyl ether, hydroquinone diallyl ether, ethylene glycol di(meth) acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols from the sugar series, or other allyl or vinyl ethers of polyfunctional alcohols, and also allyl esters of derivatives of phosphoric and/or vinylphosphonic acid, or mixtures of these compounds.

According to one preferred embodiment of the invention, the crosslinking agent is chosen from methylenebisacrylamide, allylmethacrylate or trimethylolpropane triacrylate (TMPTA). The degree of crosslinking generally ranges from 0.01 to 10 mol % and more particularly from 0.2 to 2 mol % relative to the polymer.

Among these polymers, mention may be made of:
the crosslinked AMPS copolymers described generally in document EP-A-1 069 142;
neutralized or unneutralised crosslinked copolymers comprising from 15 to 60% by weight of AMPS units and from 40 to 85% by weight of ($C_8$-$C_{16}$)alkyl (meth)acrylamide units or of ($C_8$-$C_{16}$)alkyl (meth)acrylate units relative to the polymer, such as those described in document EP-A-750 899; and
the crosslinked copolymers of partially or completely neutralized AMPS and of n-dodecylmethacrylamide, such as those described in the articles by Morishima cited above.

As more particularly suitable polymers, mention may be made of those obtained by polymerization of 2-acrylamido-2-methylpropanesulphonic acid (AMPS) or one of its sodium or ammonium salts, with an ester of methacrylic or acrylic acid, preferably an ester of methacrylic acid and of an oxyethylenated alcohol of formula (IV):

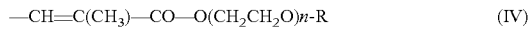

$$—CH=C(CH_3)—CO—O(CH_2CH_2O)n\text{-}R \quad \text{(IV)}$$

in which n ranges from 7 to 25, and is preferably equal to 8 or to 25, and R is an alkyl residue having from 10 to 22 carbon atoms.

As polymers of this type, mention may more especially be made of that sold under the name Aristoflex HMS by Clariant, which is a crosslinked AMPS/ethoxylated (25 EO) stearyl methacrylate copolymer, for which, in the formula (IV), n is 25 and R is $C_{16}$-$C_{18}$, or that sold under the name Aristoflex HMB by Clariant, which is a crosslinked AMPS/ethoxylated (25 EO) behenyl methacrylate copolymer, for which, in the formula (IV), n is 25 and R is $C_{22}$. It is also possible to use a blend of these polymers.

The amount of uncrosslinked amphiphilic polymer in the composition of the invention may range for example, as active material, from 0.1 to 5% by weight, preferably from 0.2 to 5% by weight, better still from 0.2 to 3% by weight relative to the total weight of the composition.

According to one advantageous embodiment, the composition according to the invention comprises:
an uncrosslinked amphiphilic polymer chosen from polymers prepared from 2-acrylamido-2-methylpropanesulphonic acid (AMPS) or one of its sodium or ammonium salts, with an ester of (meth)acrylic acid and of an oxyethylenated $C_{10}$ to $C_{20}$ alcohol comprising from 6 to 25 oxyethylenated groups; and
an organopolysiloxane elastomer obtained by reaction of dimethylvinylsiloxy-terminated dimethylpolysiloxane and of trimethylsiloxy-terminated methylhydrogenpolysiloxane, in the presence of a platinum catalyst, an amphiphilic copolymer, for example a copolymer for which the INCI name is dimethicone/vinyldimethicone copolymer (or polysilicone-11).

According to one embodiment, the above composition may also comprise a crosslinked amphiphilic polymer which may be, in particular, chosen from the hydrophobic modified crosslinked polymers of AMPS, such as for example a crosslinked AMPS/ethoxylated (25 EO) stearyl methacrylate copolymer.

Additives

The composition of the invention can also comprise one or more adjuvants. Mention may be made, as adjuvants, of gelling agents, active principles, preservatives, antioxidants, fragrances, solvents, salts, fillers, sunscreens (=UV screening agents), colouring materials, basic agents (triethanolamine, diethanolamine, sodium hydroxide) or acidic agents (citric acid), and also lipid vesicles or any other type of vector (nanocapsules, microcapsules, etc.), and mixtures thereof. These adjuvants are used in the proportions usual in the cosmetic field, for example from 0.01 to 30% of the total weight of the composition, and they are, depending on their nature, introduced into the aqueous phase of the composition or into the oily phase, or also into vesicles or any other type of vector. These adjuvants and their concentrations must be such that they do not modify the property desired for the emulsion of the invention.

Depending on the viscosity desired for the composition according to the invention, it is possible to incorporate therein one or more hydrophilic gelling agents. Mention may be made, as hydrophilic gelling agents, for example, of modified or unmodified carboxyvinyl polymers, such as the products sold under the Carbopol name (INCI name: carbomer) by Noveon; polyacrylamides; optionally crosslinked and/or neutralized polymers and copolymers of 2-acrylamido-2-methylpropanesulphonic acid, such as the poly(2-acrylamido-2-methylpropanesulphonic acid) sold by Clariant under the name "Hostacerin AMPS" (INCI name: ammonium polyacryldimethyltauramide); crosslinked anionic copolymers of acrylamide and of AMPS which are provided in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by SEPPIC; polysaccharide biopolymers, such as xanthan gum, guar gum, alginates or modified or unmodified celluloses; and mixtures thereof. When they are present, these gelling agents have to be introduced in an amount such that they do not modify the properties of the composition according to the invention. Mention may in particular be made, as lipophilic gelling agents, of modified clays, such as modified magnesium silicate (bentone gel VS38 from Rheox) or hectorite modified with distearyldimethylammonium chloride (INCI name: Disteardimonium hectorite), sold under the name "bentone 38 CE" by Rheox.

The gelling agent can be present in a content as active material ranging from, for example, 0.05% to 10% by weight and preferably from 0.1% to 5% by weight, relative to the total weight of the composition.

Mention may be made, as fillers which can be used in the composition of the invention, for example, of pigments, such as titanium, zinc or iron oxides and organic pigments; kaolin; silica; talc; boron nitride; spherical organic powders; fibres; and mixtures thereof. Mention may be made, as spherical organic powders, for example, of polyamide powders and in particular Nylon®, such as Nylon-1 or Polyamide 12, powders sold under the Orgasol names by Atochem; polyethylene powders; Teflon®; microspheres based on acrylic copolymers, such as those made of ethylene glycol dimethacrylate/lauryl methacrylate copolymer sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; polymethyl methacrylate microspheres, sold under the name Microsphere M-100 by Matsumoto or under the name Covabead LH85 by Wackherr; ethylene/acrylate copolymer powders, such as those sold under the name Flobeads by Sumitomo Seika Chemicals; or powders formed from natural organic materials, such as starch powders, in particular powders formed from crosslinked or uncrosslinked maize, wheat or rice starches, such as the powders formed from starch crosslinked with octenyl succinic anhydride sold under the name Dry-Flo by National Starch. Mention may be made, as fibres, for example, of polyamide fibres, such as in particular fibres formed from Nylon 6 (or Polyamide 6) (INCI name: Nylon 6) or from Nylon 6,6 (or Polyamide 66) (INCI name: Nylon 66) or such as fibres formed from poly(p-phenylene terephthalamide); and mixtures thereof. These fillers can be present in amounts ranging from 0 to 20% by weight and preferably from 0.5 to 10% by weight, relative to the total weight of the composition.

Mention may be made, as active principles which can be used in the composition of the invention, for example, of moisturizing agents, such as protein hydrolysates; sodium hyaluronate; polyols, such as glycerol, glycols, such as polyethylene glycols, and sugar derivatives; antiinflammatories; procyanidol oligomers; vitamins, such as vitamin A (retinol), vitamin E (tocopherol), vitamin K, vitamin C (ascorbic acid), vitamin B5 (panthenol), vitamin B3 or PP (niacinamide), the derivatives of these vitamins (in particular esters) and mixtures thereof; keratolytic and/or desquamating agents, such as salicylic acid and its derivatives, α-hydroxy acids, such as lactic acid and glycolic acid, and their derivatives, and ascorbic acid and its derivatives; urea; caffeine; depigmenting agents, such as kojic acid, hydroquinone and caffeic acid; salicylic acid and its derivatives; retinoids, such as carotenoids and vitamin A derivatives; hydrocortisone; melatonin; algal, fungal, plant, yeast or bacterial extracts; steroids; antibacterial active principles, such as 2,4,4'-trichloro-2'-hydroxydiphenyl ether (or triclosan), 3,4,4'-trichlorocarbanilide (or triclocarban) and the acids indicated above and in particular salicylic acid and its derivatives; enzymes; flavonoids; tightening agents, such as synthetic polymers, plant proteins, polysaccharides of plant origin in or not in the form of microgels, starches, wax dispersions, mixed silicates and colloidal particles of inorganic fillers; ceramides; anti-inflammatory agents; soothing agents; mattifying agents; agents for combating hair loss and/or for regrowth of the hair; antiwrinkle agents; essential oils; and mixtures thereof; and any active principle appropriate for the final objective of the composition.

The UV screening agents can be organic or inorganic (or physical UV screening agents). They can be present in an amount as active material ranging from 0.01 to 20% by weight of active material, preferably from 0.1 to 15% by weight and better still from 0.2 to 10% by weight, relative to the total weight of the composition.

Mention may be made, as examples of organic screening agents active in the UV-A and/or UV-B regions which can be added to the composition of the invention, for example, of anthranilates; cinnamic derivatives; dibenzoylmethane derivatives; salicylic derivatives, camphor derivatives; triazine derivatives such as those described in Patent Applications U.S. Pat. No. 4,367,390, EP 863 145, EP 517 104, EP 570 838, EP 796 851, EP 775 698, EP 878 469 and EP 933 376; benzophenone derivatives; β,β-diphenylacrylate derivatives; benzotriazole derivatives; benzimidazole derivatives; imadazolines; bis-benzoxazolyl derivatives, such as described in Patents EP 669 323 and U.S. Pat. No. 2,463,264; p-aminobenzoic acid (PABA) derivatives; methylenebis[(hydroxyphenyl)benzotriazole] derivatives, such as described in Applications U.S. Pat. No. 5,237,071, U.S. Pat. No. 5,166,355, GB 2 303 549, DE 19726184 and EP 893 119; screening polymers and screening silicones, such as those described in particular in Application WO 93/04665; or dimers derived from α-alkylstyrene, such as those described in Patent Application DE19855649.

The total amount of organic UV screening agents in the compositions according to the invention can range, for example, from 0.1 to 20% by weight, relative to the total weight of the composition, preferably ranging from 0.2 to 15% by weight, relative to the total weight of the composition.

Mention may be made, as physical screening agents which can be added to the composition of the invention, for example, of coated or uncoated metal oxide pigments and nanopigments, in particular titanium, iron, zirconium, zinc or cerium oxides and mixtures thereof, it being possible for these oxides to be in the form of optionally coated micro- or nanoparticles (nanopigments).

The compositions of the invention are advantageously prepared according to a process in which the oily fatty phase, comprising the oils and optionally the other fatty substances, is emulsified in the aqueous phase (into which the amphiphilic polymer has been introduced) with stirring.

According to one embodiment, the compositions of the invention are prepared according to a process in which the oily fatty phase comprising the oils and optionally the other fatty substances is emulsified in the aqueous phase (into which the amphiphilic polymer has been introduced) with gentle stirring, that is to say with a low degree of shearing. Stirring is preferably carried out with a magnetic bar or any other stirring system which gives gentle and thus low energy stirring at a temperature which can range from 20° C. to 45° C. The term "gentle stirring" is understood to mean stirring carried out with a degree of shearing of less than 1000 s$^{-1}$. Thus, the process for emulsification with gentle shearing can be carried out with any other stirring system which gives gentle and thus low energy stirring, such as, for example:
using a paddle or propeller,
in a vessel equipped with a vessel bottom turbine, with a scraping blade or with a contrarotating central mixing paddle and heating/cooling via the jacket of the vessel.

Mention may be made, as examples, of the Macef and Maxilab vessels from Olsa or the vessels provided by Pierre Guérin,
using a colloid mill,
using a static emulsifier,
with an in-line turbine, of the IKA or KMF trade mark, for example.

The compositions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for caring for (antiwrinkle, antiaging, moisturizing, antisun protection, etc.), treating, cleansing and making up keratin materials and in particular the skin, lips, hair, eyelashes and nails of human beings.

According to a preferred embodiment of the invention, the composition constitutes a cosmetic composition and is intended for topical application to the skin.

The examples which follow will make possible a better understanding of the invention without, however, exhibiting a limiting nature. The amounts shown are as % by weight, unless otherwise indicated.

EXAMPLES

Examples 1 and 2

The following emulsions are prepared:

|  | Emulsion 1 (according to the invention) | Emulsion 2 (comparative) |
|---|---|---|
| Copolymer of AMPS and of Genapol T-080 methacrylate (degree of grafting = 7.35%) (Aristoflex SNC from Clariant) containing 92% of active material in a water/alcohol mixture | 0.4% | |
| Poly(2-acrylamido-2-methylpropanesulphonic acid) crosslinked and partially neutralized with ammonium hydroxide containing 97.4% of active material in an alcohol mixture (Hostacerin AMPS from Hoechst) | 0.6% | 1% |
| Blend of α,ω-dihydroxylated polydimethylsiloxane and 5 cSt polydimethylsiloxane (12/88) (DC1503 Fluid from Dow Corning) | 2% | 2% |
| Blend of crosslinked organopolysiloxane and of cyclohexasiloxane (10/90) (Gransil RPS-6 from Grant Industries) | 25% | 25% |
| Polytetrafluoroethylene powder (12 microns) (Fluoropure 812C from Shamrock) | 1.5% | 1.5% |
| Concave silicone particles (diameter: 2.5 µm) (NLK 506 from Takemoto Oil & Fat) | 1.5% | 1.5% |
| Glycerol | 7% | 7% |
| Pentaerythrityl tetra-octanoate | 2% | 2% |
| TiO$_2$-coated mica | 0.5% | 0.5% |
| EDTA | 0.1% | 0.1% |
| Preservatives | qs | qs |
| Ethanol | 5% | 5% |
| Water | Qs for 100 | Qs for 100 |

Procedure:

The uncrosslinked amphiphilic copolymer, supplied in powder form, is dissolved in the aqueous phase (comprising the water and the glycerol) for 30 minutes with stirring at 80° C.; the solution obtained is macroscopically homogeneous.

For emulsion 1, the crosslinked amphiphilic copolymer (Hostacerin AMPS) is then added which is left to swell for 30 minutes with stirring at 80° C., then the gel obtained is left to cool.

At the same time, the α,ω-dihydroxylated polydimethylsiloxane, the preservatives, the pentaerythrityl tetraoctanoate, the silicone elastomer and then the fillers are mixed using a Rayneri mixer. Then this mixture is introduced into the aqueous gel and the whole assembly is homogenized using an in-line IKA turbine at 300 rpm for 10 minutes. Ethanol is added and the whole assembly is again homogenized using an in-line IKA turbine at 300 rpm for 10 minutes.

The macroscopic appearance and the microscopic appearance of each composition were evaluated visually according to the process indicated above, and the transmission was also evaluated visually:

|  | Emulsion 1 | Emulsion 2 |
|---|---|---|
| Visual appearance | smooth | not very smooth |
| Microscopic appearance | | coarse and heterogeneous dispersion of the oily ranges impossible to measure a globule size |
| Average size of the oily globules | around 150 µm | |
| Transmission | 46.35% | 38.55% |

These examples demonstrate that the presence of an uncrosslinked amphiphilic polymer is essential for obtaining a stable emulsion that has oily globules that are well defined and of large size. Moreover, the emulsion 1 according to the invention has a higher transmission than emulsion 2 and is therefore more translucent than the latter.

Examples 3 and 4

The following emulsions are prepared:

|  | Emulsion 3 (according to the invention) | Emulsion 4 (according to the invention) |
|---|---|---|
| Copolymer of AMPS and of Genapol T-080 methacrylate (degree of grafting = 7.35%) (Aristoflex SNC from | 0.6% | 0.45% |

| | Emulsion 3 (according to the invention) | Emulsion 4 (according to the invention) |
|---|---|---|
| Clariant) containing 92% of active material in a water/alcohol mixture | | |
| Poly(2-acrylamido-2-methylpropanesulphonic acid) crosslinked and partially neutralized with ammonium hydroxide containing 97.4% of active material in an alcohol mixture (Hostacerin AMPS from Hoechst) | 0.6% | 0.65% |
| Blend of α,ω-dihydroxylated polydimethylsiloxane and 5 cSt polydimethylsiloxane (12/88) (DC1503 Fluid from Dow Corning) | 2% | 2% |
| Blend of crosslinked organopolysiloxane and of cyclopentasiloxane (10/90) (Gransil RPS-6 from Grant Industries) | 25% | — |
| Blend of crosslinked organopolysiloxane and of cyclohexasiloxane (10/90) (Gransil RPS-6 from Grant Industries) | — | 25% |
| Caprylic/capric triglycerides/stear-alkonium hectorite/propylene carbonate (84/12/4) Myglyol gel B from Sasol | — | 1.5% |
| Polytetrafluoroethylene powder (12 microns) (Fluoropure 812C from Shamrock) | 1.5% | 1.5% |
| Concave silicone particles (diameter: 2.5 μm) (NLK 506 from Takemoto Oil & Fat) | 1.5% | 1.5% |
| Glycerol | 7% | 13% |
| Pentaerythrityl tetra-octanoate | 2% | 4% |
| TiO$_2$-coated mica | 0.5% | 0.5% |
| Water-soluble active principles | — | 10% |
| Liposoluble active principles | — | 1 |
| EDTA | 0.1% | 0.1% |
| Fragrance | —% | 0.11% |
| Preservatives | qs | qs |
| Ethanol | 5% | 5% |
| Water | Qs for 100 | Qs for 100 |

These emulsions were judged by a panel of experts to have a transparent, pearly and smooth appearance.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more." Where a modifying term is contained in parentheses, such as "(uncrosslinked) amphiphilic polymer," two things are described, one with the modifying term and one without the modifying term.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of an oil-in-water emulsion, comprising
   an oily phase,
   an aqueous phase,
   from 0.01% to 10% by weight relative to the total weight of the composition at least one uncrosslinked amphiphilic polymer which is a copolymer of 2-acrylamido-2-methylpropanesulphonic acid (AMPS) or one of its sodium or ammonium salts, with an ester of (meth)acrylic acid and a $C_{16}$-$C_{18}$ alcohol oxyethylenated with 8 mol of ethylene oxide,

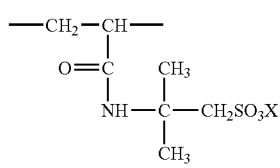

(3)

from 0.01 to 10% by weight relative to the total weight of the composition of at least one organopolysiloxane elastomer, and
   oily globules having an average size of 15 to 500 μm.

2. The composition according to claim 1, wherein the polymer has a weight-average molecular weight ranging from 10 000 to 10 000 000.

3. The composition according to claim 1, wherein the amphiphilic polymer is partially or completely neutralized by a mineral or organic base.

4. The composition according to claim 1, wherein the organopolysiloxane elastomer is chosen from those obtained:
   by a process comprising a crosslinking addition reaction of a diorganosiloxane containing at least one hydrogen bonded to the silicon and of a polyoxyalkylene having at least two ethylenically unsaturated groups;
   by a process comprising a crosslinking addition reaction of a diorganosiloxane containing at least one hydrogen bonded to the silicon and of polyglycerolated compounds having ethylenically unsaturated groups;

by a process comprising a crosslinking addition reaction of a diorganosiloxane containing at least one hydrogen bonded to the silicon and of a diorganopolysiloxane having ethylenically unsaturated groups bonded to the silicon;

by a process comprising a dehydrogenation crosslinking condensation reaction between a diorganopolysiloxane having hydroxyl end groups and a diorganopolysiloxane containing at least one hydrogen bonded to the silicon;

by a process comprising a crosslinking condensation reaction of a diorganopolysiloxane having hydroxyl end groups and of a hydrolysable organopolysilane;

by a process comprising thermal crosslinking of an organopolysiloxane; and by a process comprising crosslinking of an organopolysiloxane by high-energy radiation.

5. The composition according to claim 1, wherein the organopolysiloxane elastomer is obtained by a process comprising a crosslinking addition reaction (A) of a diorganopolysiloxane containing at least two hydrogen atoms each bonded to a different silicon atom, and (B) of a diorganopolysiloxane having at least two ethylenically unsaturated groups bonded to the silicon, especially in the presence (C) of a platinum catalyst.

6. The composition according to claim 1, wherein the organopolysiloxane elastomer is obtained by a process comprising reacting a dimethylpolysiloxane having dimethylvinylsiloxy end groups and of a methylhydrogenpolysiloxane having trimethylsiloxy end groups, in the presence of a platinum catalyst.

7. The composition according to claim 1, wherein the organopolysiloxane elastomer is a dimethicone/vinyldimethicone copolymer (or polysilicone-11).

8. The composition according to claim 1, wherein the composition further comprises a crosslinked amphiphilic polymer.

9. The composition according to claim 1, wherein the amount of oily phase is less than 40% of the total weight of the composition.

10. The composition according to claim 1, wherein the composition comprises an emulsifier content of less than or equal to 1% by weight relative to the weight of the composition.

11. A method, comprising applying a composition according to claim 1 to a keratin material.

12. The composition according to claim 1, wherein the amount of organopolysiloxane elastomer(s) ranges from 0.5 to 7% by weight relative to the total weight of the composition.

13. The composition according to claim 1, wherein the amount of organopolysiloxane elastomer(s) ranges from 1 to 4% by weight relative to the total weight of the composition.

14. The composition according to claim 1, wherein the at least one organopolysiloxane elastomer is non-emulsifying.

* * * * *